US010046288B2

(12) United States Patent
Wang et al.

(10) Patent No.: US 10,046,288 B2
(45) Date of Patent: Aug. 14, 2018

(54) VIEW DEFINITION ENHANCEMENT SYSTEM AND METHOD FOR GASTROINTESTINAL ENDOSCOPE DIAGNOSIS AND TREATMENT

(71) Applicant: Chongqing Skyforbio Co., Ltd., Chongqing (CN)

(72) Inventors: Guohua Wang, Chongqing (CN); Aling Liu, Chongqing (CN); Zhexi Wang, Chongqing (CN)

(73) Assignee: CHONGQING SKYFORBIO CO., LTD., Chongqing (CN)

( * ) Notice: Subject to any disclaimer, the term of this patent is extended or adjusted under 35 U.S.C. 154(b) by 790 days.

(21) Appl. No.: 14/397,057

(22) PCT Filed: Apr. 24, 2013

(86) PCT No.: PCT/CN2013/074621
§ 371 (c)(1),
(2) Date: Oct. 24, 2014

(87) PCT Pub. No.: WO2013/159699
PCT Pub. Date: Oct. 31, 2013

(65) Prior Publication Data
US 2015/0122294 A1    May 7, 2015

(30) Foreign Application Priority Data

Apr. 25, 2012    (CN) .......................... 2012 1 0125193

(51) Int. Cl.
*B01F 13/08*    (2006.01)
*B01F 15/06*    (2006.01)
(Continued)

(52) U.S. Cl.
CPC ............ *B01F 15/068* (2013.01); *A61B 1/015* (2013.01); *A61B 1/126* (2013.01); *A61B 1/128* (2013.01);
(Continued)

(58) Field of Classification Search
CPC ............ A61B 1/00068; A61B 1/00112; A61B 1/00119; A61B 1/00121; A61B 1/00128;
(Continued)

(56) References Cited

U.S. PATENT DOCUMENTS 2,837,320 A *  6/1958  Baron ................. A47J 43/0465
                                                              219/433
3,028,476 A *  4/1962  Hug ..................... H02K 49/108
                                                              219/201
(Continued)

FOREIGN PATENT DOCUMENTS

CN    101296648 A    10/2008
CN    201279130 Y    7/2009
(Continued)

OTHER PUBLICATIONS

International Search Report, dated Aug. 1, 2013 in connection with PCT International Application No. PCT/CN2013/074621, filed Apr. 24, 2013.
(Continued)

*Primary Examiner* — Ryan Henderson
(74) *Attorney, Agent, or Firm* — John P. White; Cooper & Dunham LLP

(57) ABSTRACT

A view definition enhancement system for gastrointestinal endoscope diagnosis and treatment (ESCGV) comprises a washing bottle (1) and a liquid delivery pipe (2) led out from the washing bottle (1). The liquid delivery pipe (2) pumps washing liquid to a liquid inlet system of a gastrointestinal endoscope or an observation window of the gastrointestinal
(Continued)

endoscope through a first peristaltic pump (3); and the washing bottle (1) is further provided with a stirring and heating subsystem capable of stirring and heating the washing liquid. A view definition enhancement method for gastrointestinal endoscope diagnosis and treatment comprises steps of: 1) adding the washing liquid into the washing bottle (1); 2) magnetically stirring the washing liquid in the washing bottle (1), and heating the washing liquid at the same time; 3) setting the temperature of the washing liquid to 25-38° C.; and 4) delivering the washing liquid into the observation window of the gastrointestinal endoscope. The ESCGV can enhance the view definition under the gastrointestinal endoscope, make the operation simple and convenient, reduce the missed diagnosis and erroneous diagnosis, and improve the treatment quality of the gastrointestinal endoscope.

8 Claims, 8 Drawing Sheets

(51) Int. Cl.
    *A61B 1/00* (2006.01)
    *A61B 1/12* (2006.01)
    *A61B 1/015* (2006.01)
    *A23G 9/12* (2006.01)
    *A47J 27/00* (2006.01)
    *A61M 3/02* (2006.01)

(52) U.S. Cl.
    CPC ............ *B01F 13/08* (2013.01); *B01F 15/065* (2013.01); *A23G 9/12* (2013.01); *A47J 27/004* (2013.01); *A61M 3/0258* (2013.01)

(58) Field of Classification Search
    CPC ........... A61B 1/015; A61B 1/12; A61B 1/121; A61B 1/123; A61B 1/125; A61B 1/126; A61B 1/127; A61B 1/128; A61M 1/0058; A61M 3/0233; A61M 3/025; A61M 3/0254; A61M 3/0258; A47J 25/004; A23G 9/12; B01F 15/065; B01F 15/068; B01F 13/08; A21B 7/005
    See application file for complete search history.

(56) References Cited

U.S. PATENT DOCUMENTS

| | | | | |
|---|---|---|---|---|
| 3,433,465 A | * | 3/1969 | Szpur | B01F 13/0818 219/433 |
| 3,766,360 A | * | 10/1973 | Eddleman | B01L 7/00 219/415 |
| 4,568,192 A | * | 2/1986 | Kudermann | B01F 13/0818 219/433 |
| 5,178,606 A | | 1/1993 | Ognier et al. | |
| 5,834,739 A | * | 11/1998 | Lockwood | A47J 43/0465 219/433 |
| 2006/0146645 A1 | * | 7/2006 | Rosener | B01F 13/0818 366/274 |
| 2006/0266423 A1 | | 11/2006 | Akiba et al. | |
| 2007/0221068 A1 | * | 9/2007 | Boussemart | A47J 27/004 99/279 |
| 2007/0257021 A1 | * | 11/2007 | Lockwood | B01L 7/00 219/443.1 |
| 2009/0116333 A1 | * | 5/2009 | Lu | B01D 3/02 366/145 |
| 2011/0103175 A1 | * | 5/2011 | Waldmann | G01G 3/14 366/141 |
| 2011/0232506 A1 | * | 9/2011 | Cai | A47J 43/046 99/484 |
| 2012/0095293 A1 | * | 4/2012 | Bendele | A61B 1/00119 600/158 |
| 2013/0152982 A1 | * | 6/2013 | Tanaka | A61B 1/123 134/115 R |

FOREIGN PATENT DOCUMENTS

| | | | | |
|---|---|---|---|---|
| CN | 101596181 A | * | 12/2009 | ........... A61K 31/198 |
| CN | 101627894 A | | 1/2010 | |
| CN | 101828936 A | | 9/2010 | |
| CN | 102631179 A | | 8/2012 | |
| CN | 202554588 U | | 11/2012 | |
| JP | 07031584 A | * | 2/1995 | ............. A61B 1/015 |
| JP | 2009226082 A | * | 10/2009 | ............. A61B 1/015 |
| JP | WO 2012035776 A1 | * | 3/2012 | ............. A61B 1/123 |

OTHER PUBLICATIONS

Written Opinion of the International Searching Authority, dated Aug. 1, 2013, in connection with PCT International Application No. PCT/CN2013/074621, filed Apr. 24, 2013.

International Preliminary Report on Patentability, dated Oct. 28, 2014, in connection with PCT International Application No. PCT/CN2013/074621, filed Apr. 24, 2013.

* cited by examiner

VIEW DEFINITION ENHANCEMENT SYSTEM AND METHOD FOR GASTROINTESTINAL ENDOSCOPE DIAGNOSIS AND TREATMENT

CROSS-REFERENCE TO RELATED APPLICATIONS

This application is a § 371 national stage of PCT International Application No. PCT/CN2013/074621, filed Apr. 24, 2013, claiming priority of Chinese Patent Application No. 201210125193.4, filed Apr. 25, 2012, the contents of each of which are hereby incorporated by reference in their entirety.

TECHNICAL FIELD

The present application relates to the technical field of medical treatment and public health, in particular, to the field of inspection diagnosis and treatment of gastroscope and enteroscope.

BACKGROUND

Currently, in the field of medical treatment and public health, there are many devices for gastrointestinal endoscope diagnosis and treatment. When clinicians operate these devices, the field of view may not be clear. The reason for that is, some patients may have too much foam, mucus, blood or excreta in the gastrointestinal tract depending on various conditions of the patients. The observation from the field of view of gastrointestinal endoscope is thus hindered, which will increase the difficulty in doctors' diagnosis. It is also not beneficial to inspect the disease effectively in good time, as well as to make a treatment precisely. Since repeated observations are required, patient's suffering and the working intensity for the doctor will be increased.

When performing the gastrointestinal endoscope diagnosis and treatment, a washing device is usually adopted. Such washing device is capable of supplying saline based on the actual clinician needs. By washing part of the gastrointestinal tract with the supplied saline, people expect to achieve an improved definition of the field of view of the gastrointestinal endoscope, but the effect is usually not satisfying. When in use, the above mentioned water supplying device needs to be operated by specific personnel with his/her hand. It is not easy to control the flow rate and washing time. If the flow rate is too high and the washing time is too long, too much liquid will be accumulated in the patient's body, which makes the patient to feel nausea and vomiting. Too much liquid backflow may enter into the trachea, which increases the patient's risk.

The Chinese Patent No. CN201020567721.8 filed on May 4, 2011 discloses a closed type flushing device comprising a disposable sterilization washing ball and a water intake pipe with a regulating valve. The water intake pipe is connected with the disposable washing ball. The closed type water flushing device has a high aseptic degree, wherein an enclosed system is formed by the washing ball and the water intake pipe. Saline flows into the surgery field through the enclosed system without exposing itself to the air, which thereby reduces the chance of infection and postoperative infection probability and improves the operation quality. But when in use, this flushing device also requires specific personnel to operate with his/her hands which increases the labor cost. In addition, the adjustment of the flow can only be made by feeling, thus the flow rate is not constant, which increases the discomfort and the risk for the patient. The regulating valve needs to be opened repeatedly to introduce liquid after the liquid is run out, which distracts the doctor from the field of view and brings risk to the diagnosis and treatment procedure. Moreover, it is required to supplement liquid at all times, which interrupts the operation and brings discomfort to the patient.

Clinically, in some gastrointestinal endoscope inspection, when the doctor needs to use the washing device, a common high volume syringe connected with a catheter is typically adopted directly. Saline is employed as the washing liquid. But this device also has the some disadvantages, such as the adjustment of the flow can only be made by feeling; the flow rate is not constant, which requires specific personnel to operate it; the waiting time for washing is long; the amount of washing liquid is high; the operating time for gastrointestinal endoscope inspection is long; the temperature of the washing liquid is low in winter; and the irritation is strong. In clinical use, the device takes about 15 minutes for the gastrointestinal endoscope inspection.

The present application is proposed in view of the above problems.

SUMMARY

One object of the present application is to provide a view definition enhancement system for gastrointestinal endoscope diagnosis and treatment, abbreviated as ESCGV. The term gastrointestinal endoscope of this disclosure refers to general term for gastroscope and enteroscope. A person skilled in the art can understand that gastrointestinal endoscope itself refers to the gastroscope or enteroscope or an integrated means of both for gastrointestinal check.

To achieve the above objects, the technical solution of the present application is as follows. A view definition enhancement system for gastrointestinal endoscope diagnosis and treatment, comprises a washing bottle (1) and a liquid delivery pipe (2) led out from the washing bottle (1), wherein the liquid delivery pipe (2) pumps washing liquid to a liquid inlet system of a gastrointestinal endoscope or an observation window of the gastrointestinal endoscope through a first peristaltic pump (3), the washing bottle (1) is provided with a stirring and heating subsystem capable of stirring and heating the washing liquid.

The washing liquid of this disclosure is composed of solvent and a washing agent A, and the washing agent A consists of dimeticone/simethicone and glucose, wherein glucose is 15-250 parts, dimeticone or simethicone is 1-20 parts; wherein the solvent is saline or sterile water or pure water or glucose injection with the concentration of 5% and ratio between the mass of the dimeticone or simethicone and the volume of the solvent is calculated to be 0.01-1% in unit of g/ml.

The stirring and heating subsystem of this disclosure comprises a heating means and a stirring means, wherein the heating means comprises a heating plate heating means, a heating cup heating means or a water bath heating means; the stirring means comprises a magnetic stirring means, a second peristaltic pump stirring means or stirring paddle stirring means. Those skilled in this art can understand that all of the aforementioned heating means and stirring means are able to achieve ideal heating and stirring effects. Therefore, the stirring and heating subsystem of this disclosure may be the combination of any of the heating means and the stirring means as mentioned above.

Adopting the above technical solutions, the washing bottle for accommodating the washing liquid can be sterilized and used repeatedly and can withstand the steam sterilization disinfection, which saves the cost and ensures the safety for the user. The stirring and heating subsystem stirs the washing liquid in the washing bottle to mix the washing liquid evenly so as to ensure the washing liquid is available at any time; meanwhile the stirring and heating subsystem heats the washing bottle and keeps it at a constant temperature such that the temperature of the washing liquid in the washing bottle is uniform and close to the temperature in the human gastrointestinal tract. In this case, when the washing liquid flows into the patient body, it will not bring irritation to the patient, hence improve the comfort level for the patient. The inlet end of the liquid delivery pipe is connected to the washing bottle and the outlet end is directly connected to the water inlet system of the gastrointestinal endoscope or the observation window of the gastrointestinal endoscope. The middle end passes through the first peristaltic pump.

According to the view definition enhancement system for gastrointestinal endoscope diagnosis and treatment of this disclosure, the range of bearable pressure of the liquid delivery pipe is 6-8 kg/cm$^2$. Under this pressure, the liquid delivery pipe will not rupture in the case of blocking, hence the cross contamination is avoided. The adjustable range of the flow rate of the first peristaltic pump is 0-900 ml/min and the maximum flow rate is limited at 900 ml/min, which avoids the discomfort made to the patient caused by providing too much water during the water pumping process by the first peristaltic pump. The pressure range of the liquid delivery pipe at the water outlet is 0-3 kg/cm$^2$. Such pressure ensures the smooth flow of the washing liquid, meanwhile avoids the wounds exacerbation at the location for therapy or other discomfort caused due to the excessive pressure.

According to the present application, after the adjustment of the system, the switch of the first peristaltic pump is switched off, which makes the washing liquid in the standby mode. If needed, the switch of the first peristaltic pump is switched on, therefore, the first peristaltic pump can pump the washing liquid out of the washing bottle, flow the washing liquid to the therapy window of the gastrointestinal endoscope through the liquid delivery pipe, hence wash the location for therapy in the patient's body to improve the view definition for the gastrointestinal endoscope diagnosis and treatment. The system of this disclosure may be operated by one clinician during gastrointestinal endoscope diagnosis and treatment. Additional specific personnel are not required, thus saving the labor cost during the operation. The flow and flow rate in the present application are controllable, which thus improves the promptness and the accuracy for the water supply during the operation of the gastrointestinal endoscope therapy device, thus avoids to distract the doctor from the field of view and eliminates the risk occurred during the therapy, and meanwhile the comfort of the patient is ensured.

As one of the embodiment of the present application, the stirring and heating subsystem is the heating plate heating means plus the magnetic stirring means, in particular, comprises a heating plate (4), a heat insulation pad (5), a locating block (6), a permanent magnet (7), a supporting frame (8), an electric motor (9) and a magnetic inducting block (10), wherein, the heating plate (4) is located below the washing bottle (1) and supported by the heat insulation pad (5) which is fixed to the locating block (6); an accommodating hole is provided in the center of the heat insulation pad (5) and the permanent magnet (7) is provided in the accommodating hole; the permanent magnet (7) is installed on the supporting frame (8), the lower end of which is connected to the output shaft of the electric motor (9); a magnetic inducting block (10) cooperating with the permanent magnet (7) is provided over the permanent magnet (7) and is installed at the center of the bottom of the washing bottle (1).

In the above structure, the magnetic inducting block wrapped by a layer of Teflon in the periphery can be sterilized and used repeatedly. The supporting frame and the permanent magnet are rotated by the output shaft of the electric motor. With the cooperation with the magnetic inducting block, the permanent magnet performs the magnetic stir to the washing liquid in the washing bottle and mixes the washing liquid evenly so as to ensure the washing liquid is available at any time. At the same time, the rotating part of the stirring and heating subsystem is not in contact with the washing liquid, thus can effectively avoids the contamination from the washing liquid. The integrated structure of the rotating portion and the heating portion makes the whole stirring and heating subsystem compact in structure, small in size, an easy-to-assemble and a low-cost.

The stirring and heating subsystem of the disclosure, a first temperature sensor (11) is provided next to the heating plate (4), a second temperature sensor (12) is provided in the washing bottle (1) and the top part of the second sensor (12) is fixed to the bottle cap of the washing bottle (1). The first temperature sensor is used for monitoring the temperature of the heating plate and the second temperature sensor is used for monitoring the temperature of the washing liquid within the washing bottle. The first temperature sensor is connected to the second temperature via the control circuit. The two temperature sensors cooperate with each other, which keeps the washing liquid at a temperature that is adapted to the target temperature required by the therapy. The target temperature may be set between 25° C. to 38° C., which ensures the automaticity and accuracy of the temperature control as well as the comfort of the patient when the washing liquid enters into the human body.

The stirring and heating subsystem of the disclosure, two permanent magnets (7) are provided symmetrically in the accommodating hole located at the center of the heat insulation pad (5) and the two permanent magnets (7) are both embedded in the upper part of the supporting frame (8), which facilitates the installation and the replacement of the permanent magnets, thus is beneficial to industrial production.

The stirring and heating subsystem of the disclosure, the washing bottle (1), the heating plate (4), the heat insulation pad (5), the locating block (6), the permanent magnet (7), the supporting frame (8) and the electric motor (9) are arranged in the same housing (13) and the liquid delivery pipe (2) extends from the housing (13). Such above structure integrates the heating with the stirring, thus saving the space of the device.

The stirring and heating subsystem of the disclosure, the heating plate (4), the heat insulation pad (5), the locating block (6), the permanent magnet (7), the supporting frame (8) and the electric motor (9) are arranged in the same base (14) and the washing bottle (1) is supported by the base (14). Due to the above structure, the contacting distance between the washing bottle and the permanent magnet is short, facilitating the interaction of the magnetic inducting block within the washing bottle with the permanent magnet so as to ensure the effect of magnetic stir.

As the second embodiment of the present application, the stirring and heating subsystem is the heating cup heating means plus the magnetic stirring means, in particular it comprises: a heating cup (28), a PTC heater (29), a locating block (6), a permanent magnet (7), a supporting frame (8), an electric motor (9) and a magnetic inducting block (10); the heating cup (28) is located below the washing bottle (1) and the PTC heaters (29) are fixed at the bottom of the heating cup (28) and surrounding the heating cup (28); the PTC heater (29) is wrapped around by a heat preservation layer (30) and the heating cup (28) is fixed on the locating block (6); in the center of the locating block (6) is provided an accommodating hole in which a permanent magnet (7) is arranged; the permanent magnet (7) is installed on the supporting frame (8) and the lower part of the supporting frame (8) is connected to the output shaft of the electric motor (9); an magnetic inducting block (10) cooperating with the permanent magnet (7) is provided over the permanent magnet (7) and is installed in the center of the bottom of the washing bottle (1).

Wherein, a temperature sensor (31) is provided within the washing bottle (1) and is fixed to the bottom of the washing bottle (1); in the center of the locating block (6) an accommodating hole is provided in which two permanent magnets (7) are arranged symmetrically; both permanent magnets (7) are embedded in the upper part of the supporting frame (8).

The PTC heater of the disclosure is a well-known structure in the prior art, herein specific definition will not be given.

The washing bottle (1), the heating cup (28), the PTC heater (29), the heat preservation layer (30), the locating block (6), the permanent magnet (7), the supporting frame (8) and the electric motor (9) are located within the same housing (13) and the liquid delivery pipe (2) extends from the housing (13); the heating cup (28), the PTC heater (29), the heat preservation layer (30), the locating block (6), the permanent magnet (7), the supporting frame (8) and the electric motor (9) are connected to the housing (13) via a supporting shaft (32) and the washing bottle (1) is installed within the heating cup (28).

As the third embodiment of the present application, the stirring and heating subsystem is the heating cup heating means plus the second peristaltic pump means, in particular it comprises: a heating cup (28), a locating block (6), a second peristaltic pump (23) and a circulating tube (22); the washing bottle (1) is located within the heating cup (28) and fixed on the locating block (6); a second peristaltic pump (23) is provided outside the washing bottle (1) and a circulating tube (22) pass over the second peristaltic pump (23); the liquid inlet and the liquid outlet of the circulating tube (22) are both located within the washing bottle (1), wherein the liquid inlet is near the bottom of the washing bottle (1) and the liquid outlet is near the opening of the bottle (1).

As the fourth embodiment of the present application, the stirring and heating subsystem is the heating plate heating means plus the second peristaltic pump means, in particular it comprises: a heating plate (4), a heat insulation pad (5), a locating block (6), a circulating tube (22) and a second peristaltic pump (23); the heating plate (4) is located below the bottom of the washing bottle (1) and is supported by the heat insulation pad (5) which is fixed on the locating block (6); a second peristaltic pump (23) is provided outside the washing bottle (1) and a circulating tube (22) passes over the second peristaltic pump (23); the liquid inlet and the liquid outlet of the circulating tube (22) are both located within the washing bottle (1), wherein the liquid inlet of the circulating tube (22) is near the bottom of the washing bottle (1) and the liquid outlet of the circulating tube (22) is near the opening of the bottle (1).

The above structure employs the heating plate for the heating and the second peristaltic pump for the stirring. By the circulation in the second peristaltic pump, the washing liquid in the washing bottle is in a uniformly stirred state. During such stir, the washing liquid within the washing bottle can be mixed evenly due to the eddy formed by the power generated by the flow of the washing liquid itself without adopting any other power source, which thereby avoids the cross contamination caused by other power sources. In addition, the second peristaltic pump is arranged outside the washing bottle making the structure of the washing bottle simpler.

As the fifth embodiment of the present application, the stirring and heating subsystem is the water bath heating means plus the second peristaltic pump means, in particular it comprises: a circulating tube (22), a second peristaltic pump (23) and a thermostatic water bath heating means (24), the second peristaltic pump (23) and the thermostatic water bath heating means (24) are provided outside the washing bottle (1); the circulating tube (22) passes through the thermostatic water bath heating means (24), and then passes through the second peristaltic pump (23); the liquid inlet and the liquid outlet of the circulating tube (22) are both located within the washing bottle (1), wherein the liquid inlet of the circulating tube (22) is near the bottom of the washing bottle (1) and the liquid outlet of the circulating tube (22) is near the opening of the bottle (1).

The uniform stir and mix provided by the above structure still adopts the second peristaltic pump, which is able to avoid the contamination of the washing liquid. The above structure adopts water bath heating means and heats the circulating tube via the water bath. The heat is conducted to the washing liquid by the circulating tube so as to control the temperature of the washing liquid in the washing bottle. By way of water bath, the heating means is more moderate and the temperature fluctuation range is small. In addition, because the water bath heating is conducted outside the washing bottle, the structure of the washing bottle is simpler.

As the sixth embodiment of the present application, the stirring and heating subsystem is the water bath heating means plus the magnetic stirring means, in particular it comprises: a water bath heating vessel (25), a heating plate (4), a heat insulation pad (5), a permanent magnet (7), a supporting frame (8), an electric motor (9), a magnetic inducting block (10) and a magnetic inductor (26); a water bath heating vessel (25) is installed in the washing bottle (1) and a magnetic inducting block (10) is fixed in the center of the bottom of the washing bottle (1); a magnetic inductor (26) is installed in the center of the bottom of the water bath heating vessel (25) and a heating plate (4) supported by the heat insulation pad (5) is arranged below the magnetic inductor (26); an accommodating hole is provided in the center of the heat insulation pad (5) and inside the hole a permanent magnet (7) is provided; the permanent magnet (7) is installed on the supporting frame (8), the lower end of which is connected to the output shaft of the electric motor (9).

The above structure adopts the water bath heating means which is able to diminish the temperature fluctuation of the washing liquid. The even mixture of the washing liquid is achieved by the magnetic stir. A magnetic inductor is also provided in the water bath such that the liquid in the water bath heater can be stirred and mixed evenly. Therefore, the water bath temperature outside the whole washing bottle is all around consistent and the heat conduction is kept uniform. The magnetic inductor in the water bath heating vessel and the magnetic inducting block in the washing bottle can move simultaneously under the drive of the same permanent magnet, hence the structure is simpler.

In order to simplify the structure, facilitate the manufacture and assembly as well as reduce the cost, the present application further provides the seventh embodiment, the stirring and heating subsystem is the heating plate heating means plus the stirring paddle stirring means, in particular it comprises: a heating plate (4), an electric motor (9) and a stirring paddle (27); the heating plate (4) is installed at the bottom of the washing bottle (1) and a stirring paddle (27) connected to the output shaft of the electric motor (9) is provided within the washing bottle (1); the electric motor (9) is provided outside the washing bottle (1).

With regard to the aforementioned technical solutions, the switch of the first peristaltic pump (3) of this disclosure is a foot switch (15) which is connected to the first peristaltic pump (3) via the control circuit. The foot switch (15) is connected with a timing switch which is connected in series in the control circuit of the foot switch (15). The actuating force of the foot switch is less than 45 N. When the clinician stamps on the foot switch, the foot switch is switched on and the first peristaltic pump starts working. When the foot is moved away, the first peristaltic pump stops working. If the clinician forgets to remove his/her foot from the foot switch, the foot switch is controlled by the timing switch with a longest turn-on time of 15-20 seconds, preferably 18 seconds. Thereby, the operating time of the first peristaltic pump can be controlled no longer than the longest turn-on time, during which the maximum amount of the one-time water supply can be controlled. Hence it avoids the discomfort of the gaseous distention made to the patient caused by providing too much water at a time.

The second aim of this present application is to provide a view definition enhancement method for gastrointestinal endoscope diagnosis and treatment.

To achieve the above aims, the technical solutions are described as follows. A view definition enhancement method for gastrointestinal endoscope diagnosis and treatment utilizing the view definition enhancement system for gastrointestinal endoscope diagnosis and treatment comprises the following steps:
1) adding the washing liquid to the washing bottle (1);
2) switching on the stirring and heating subsystem, at the time that the washing liquid in the washing bottle (1) is heated, stirring the washing liquid within the washing bottle (1) to mix the washing liquid evenly;
3) maintaining the temperature of the washing liquid in the washing bottle (1) at 25-38° C.;
4) turning on the switch of first peristaltic pump (3) to make the first peristaltic pump (3) pump out the washing liquid in the washing bottle (1); the washing liquid flows to the water inlet system or the observation window of the gastrointestinal endoscope through the liquid delivery pipe (2) and washes the location for therapy in the patient's body for observation.

The above method could supply the washing liquid adapted to the temperature of the human body into the patient's body so as to wash the observation window of the gastrointestinal endoscope and enhance the view definition in the gastrointestinal endoscope, and thereby facilitate the therapy for the clinician. Meanwhile, during the washing of the observation window of the gastrointestinal endoscope, it will not bring stimulation to the patient, hence ensure the comfort for the patient.

According to the view definition enhancement method for gastrointestinal endoscope diagnosis and treatment of this disclosure, the washing liquid is in the range of 450-2000 ml.

According to the view definition enhancement method for gastrointestinal endoscope diagnosis and treatment of this disclosure, the range of the bearable pressure of the liquid delivery pipe (2) is 6-8 kg/cm$^2$ and the range of the pressure of the liquid delivery pipe at the water outlet is 0-3 kg/cm$^2$.

According to the view definition enhancement method for gastrointestinal endoscope diagnosis and treatment of this disclosure, the adjustable range of the flow rate of the first peristaltic pump (3) is 0-900 ml/min, and the maximum flow rate is controlled at 900 ml/min.

According to the view definition enhancement method for gastrointestinal endoscope diagnosis and treatment of this disclosure, the flow rate of the washing liquid does not exceed 900 ml/min.

The washing liquid of this disclosure is composed of a solvent and a washing agent A, where the washing agent A consists of dimeticone or simethicone and glucose, wherein glucose is 15-250 parts, dimeticone or simethicone is 1-20 parts. The ratio between the mass of the dimeticone or simethicones and the volume of the solvent is calculated to be 0.01-1% in the unit of g/ml, and preferably 0.15%. In the range of the above mixing ratio, not only the defoaming ability is guaranteed but also the time required for mixing the washing liquid evenly is saved. More importantly, in the precondition that the therapy quality can be ensured, the washing time can be shortened and the amount of washing liquid will be reduced, which thereby both boosts the therapy efficiency and improves the compliance and comfort of the patient. Meanwhile, the above materials are selected to facilitate the preparation of the washing agent A. With such ratios, the washing agent A of excellent liquidity and suitability for filling may be prepared without any other auxiliary materials, and thereby reducing the manufacturing cost effectively.

Regarding to the washing liquid in this disclosure, the solvent is saline or sterile water or pure water or glucose injection with the concentration of 5%. In this case, on one hand the material can be obtained easily and the cost is low, on the other hand, the washing agent can be mixed better with the solvent.

According to the view definition enhancement method for gastrointestinal endoscope diagnosis and treatment of the present application, the patient takes a pack of washing agent B 15-30 minutes before the gastrointestinal endoscope diagnosis and treatment begins; the washing agent B is composed of dimeticone or simethicone and glucose, wherein glucose is 15-250 parts, dimeticone or simethicone is 1-20 parts; the content range of dimeticone or simethicone in a pack of washing agent B is 40 mg-500 mg/pack. The reason for taking the washing agent B is to eliminate most of the foam or bubble within the human body so as to get prepared for the gastrointestinal endoscope diagnosis and treatment and to avoid the washing during therapy as much as possible. It is convenient to prepare the washing agent B with the above composition. With such ratio, the washing agent B of excellent liquidity and suitablility for filling may be prepared without any other auxiliary materials, which thereby reduces the manufacturing cost effectively.

In addition, the view definition enhancement method for gastrointestinal endoscope diagnosis and treatment realizes the control to the switch of the first peristaltic pump via the foot switch or the combination of the foot switch with the timing switch, and the timing switch assists to set the turn-on time to be 15-20 seconds, and preferably 18 seconds.

The advantageous effects of the present application are described as follows.

(1) The view definition enhancement system for gastrointestinal endoscope diagnosis and treatment may be operated by one single clinician during gastrointestinal endoscope diagnosis and treatment. Specific personnel are not additionally required, which saves the labor cost.
(2) The control by the foot switch makes the operation simple and convenient which may be manipulated by one single clinician, which enhances the promptness and the accuracy of washing during the operation.
(3) The supply of liquid can be provided or stopped at any time as needed. Depending on the various types of liquid, the heating and/or the magnetic stirring may be used, which increases the applicability for the samples in the system.
(4) The time of therapy can be significantly reduced and the compliance and comfort of the patient can be greatly enhanced. When each patient is treated with gastrointestinal endoscope diagnosis and treatment, the view definition is dramatically improved under the gastrointestinal endoscope, which thereby reduces the missed diagnosis and erroneous diagnosis and improves the treatment quality of the gastrointestinal endoscope.

LIST OF REFERENCE NUMBERS

Figure 1:
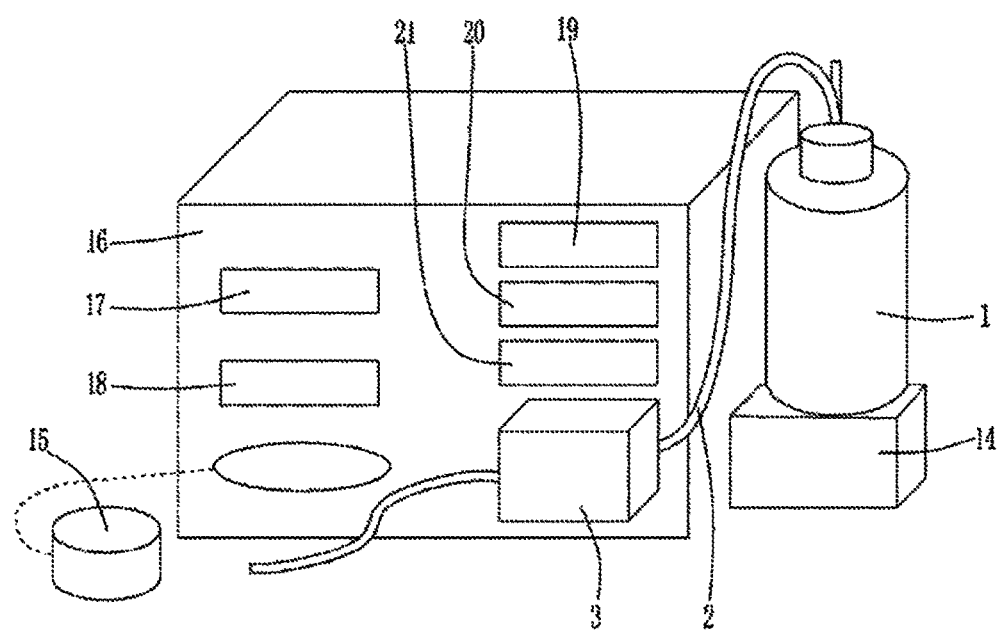
FIG. 1 is a schematic view of the structure of the view definition enhancement system for gastrointestinal endoscope diagnosis and treatment and a schematic view of the first embodiment of the stirring and heating subsystem.

1: washing bottle;
2: liquid delivery pipe
3: first peristaltic pump
4: heating plate
5: heat insulation pad
6: locating block
7: permanent magnet
8: supporting frame
9: electric motor
10: magnetic inducting block
11: first temperature sensor
12: second temperature sensor
13: housing
14: base
15: foot switch
16: electric cabinet
17: power switch
18: flow regulating switch
19: magnetic stirring switch
20: stirring speed regulating switch
21: heating thermostatic switch
22: circulating tube
23: second peristaltic pump
24: thermostatic water bath heating means
25: water bath heating vessel
26: magnetic inductor
27: stirring paddle
28: heating cup
29: PTC heater
30: heat preservation layer
31: temperature sensor

DETAILED DESCRIPTION OF THE PREFERRED EMBODIMENTS

The embodiments below are given to illustrate the present application without limiting the scope of the present application.

Embodiment 1

Figure 2:
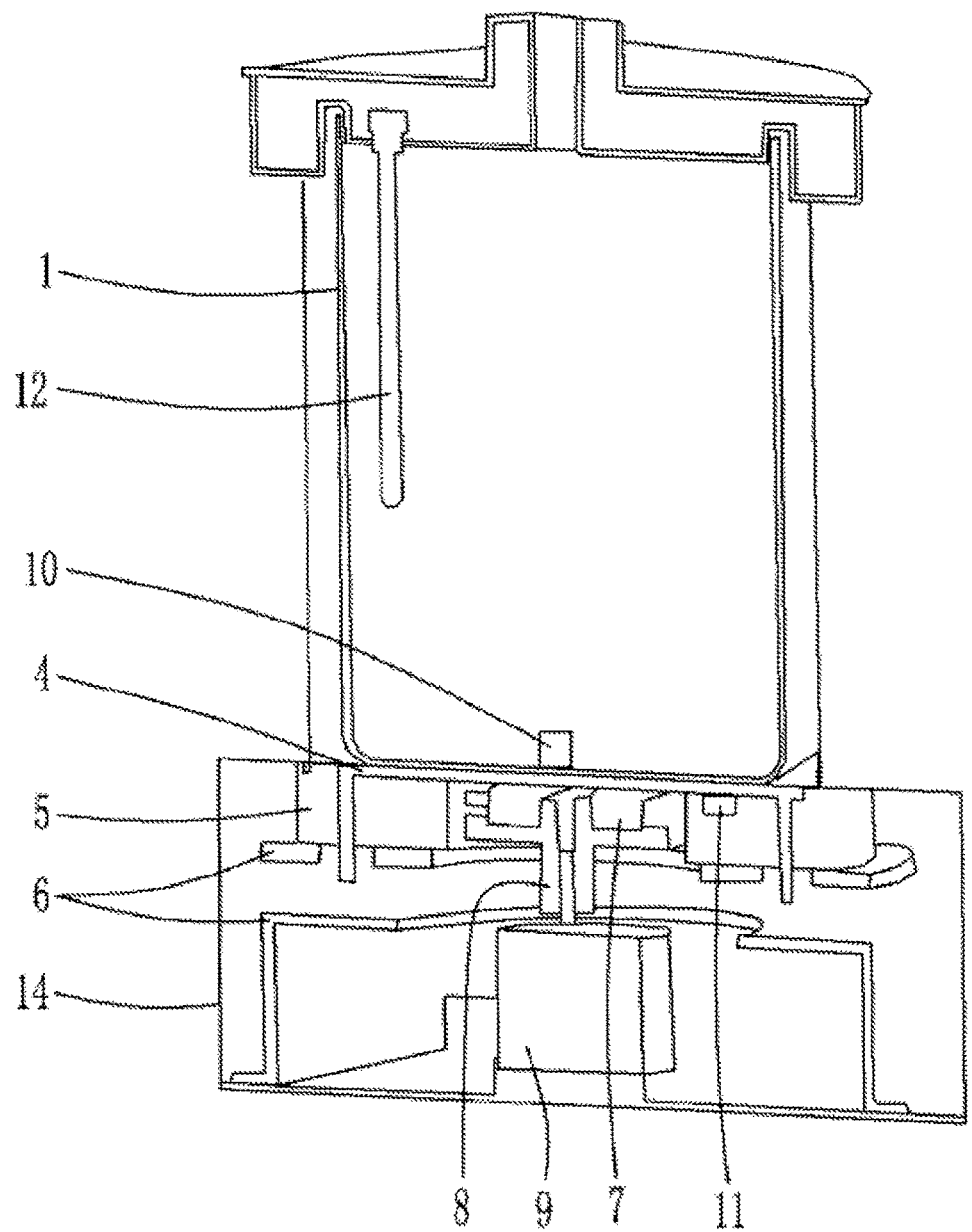
FIG. 2 is a schematic view in which each component below the washing bottle is arranged in the same base in the first embodiment.
Figure 3:
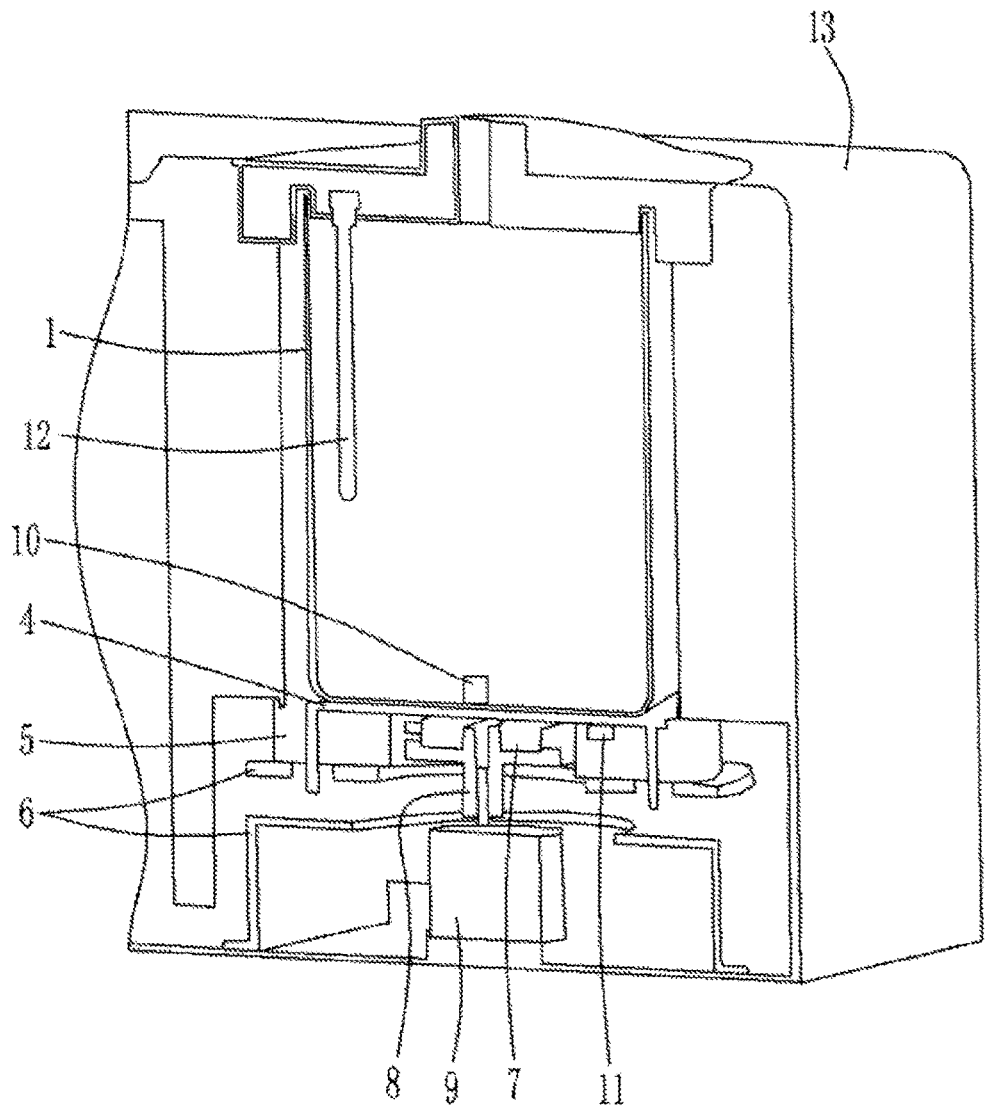
FIG. 3 is a schematic view in which the washing bottle and each component below the washing bottle are arranged in the same base in the first embodiment.

As shown in FIGS. 1, 2, 3, this embodiment provides a view definition enhancement system for gastrointestinal endoscope diagnosis and treatment composed of a washing bottle 1, a liquid delivery pipe 2, a first peristaltic pump 3, a heating plate 4, a heat insulation pad 5, a locating block 6, a permanent magnet 7, a supporting frame 8, an electric motor 9, a magnetic inducting block 10, a first temperature sensor 11, a second temperature sensor 12, a foot switch 15 and an electric cabinet 16 etc.

As shown in FIG. 2 and in combination with FIG. 1, the heating plate 4, the heat insulation pad 5, the locating block 6, the permanent magnet 7, the supporting frame 8, the electric motor 9 are arranged in the same base 14 which preferably is in the shape of cuboid or other appropriate shapes. An electric motor 9 is installed in the middle of the lower part within the base 14 with the output shaft thereof standing upward. The output shaft of the electric motor 9 extends into the lower end of the supporting frame 8, and both of which are fixedly connected with each other. Two permanent magnets 7 are embedded in the upper part of the supporting frame 8, both of which are provided symmetrically at the same height. The upper part of the supporting frame 8 together with the two permanent magnets 7 is disposed in the accommodating hole in the middle of the heat insulation pad 5. The bottom of the heat insulation pad 5 is fixed and supported by the locating block 6 which is fixedly connected to the base 14 or integrated with the base 14 as a whole. A heating plate 4 composed of the body and the supporting legs is provided on the heat insulation pad 5. The body of the heating plate 4 is supported by the heat insulation pad 5 and is adjacent to the inner upper wall of the base 14 and the supporting legs of the heating plate 4 are embedded downward into the heat insulation pad 5 and the locating block 6.

As shown in FIG. 2 and in combination with FIG. 1, the washing bottle 1 for accommodating washing liquid is supported at the bottom by the upper surface of the base 14. Preferably, the washing bottle 1 is beaker. The opening of the upper end is sealed by the bottle cap and a second temperature sensor 12 is provided in the washing bottle 1. The top part of the second temperature sensor 12 is fixed to the bottle cap of the washing bottle 1. A first temperature sensor 11 for monitoring the temperature of the heating plate 4 is provided near the heating plate 4 and the second temperature sensor 12 is used for monitoring the temperature of the washing liquid within the washing bottle 1. The first temperature sensor 11 is connected to the second temperature 12 via the control circuit. The two temperature sensors cooperates with each other and maintains the temperature of the washing liquid within the range of 25-38° C. corresponding to the human body temperature. A magnet inducing block 10 cooperating with the permanent magnet 7 is provided on the washing bottle 1. The magnet inducing block 10 is embedded in the center of the bottom of the washing bottle 1 and essentially right above the permanent magnet 7. When the permanent magnet 7 is rotated by the output shaft of the electric motor 9, the permanent magnet 7 cooperates with the magnetic inducting block 10 and generates a magnet field to perform a magnet stir to the washing liquid within the washing bottle 1 in order to protect the washing liquid from pollution.

As shown in FIG. 1, a liquid delivery pipe 2, preferably a rubber pipe, is connected to the washing bottle 1, extended from the washing bottle 1, and through the first peristaltic pump 3. The exit of the liquid delivery pipe 2 is connected to the inflow system of the gastrointestinal endoscope or directly connected to the observation window of the gastrointestinal endoscope. The switch of the first peristaltic pump 3 is a foot switch 15 which is connected to the first peristaltic pump 3 via the control circuit. A timing switch connected in series in the control circuit is connected to the foot switch. When the clinician stamps on the foot switch 15 with his/her foot, the foot switch is switched on and the first peristaltic pump 3 starts to work. When the foot is moved away, the first peristaltic pump 3 stops working. The timing switch is used to control the foot switch 15. The turn-on time for one time switching of the foot switch 15 is 18 seconds. It should be noted that the turn-on time for one time switching of the foot switch 15 can be adjusted as needed. If the clinician forgets to remove his/her foot from the foot switch 15, the foot switch 15 will be switched off automatically after 18 seconds. Thereby, the operating time of the first peristaltic pump 3 could be controlled within 18 seconds each time, thus it will control the maximum amount of the one time water supply, and hence avoid the discomfort of the gaseous distention made to the patient caused by providing too much water at a time.

As shown in FIG. 1, the first peristaltic pump 3 is located within or near the electric cabinet 16 which is closely next to the washing bottle 1. The control circuits of the first peristaltic pump 1, the heating plate 4, the electric motor 9, the first temperature sensor 11, the second temperature sensor 12 and the foot switch 15 are all arranged within the electric cabinet 16. A power switch 17 for controlling the power supply of the overall system, a flow regulating switch 18 for controlling the work of the first peristaltic pump 3, a magnetic stirring switch 19 for controlling the switch on of the electric motor 9, a stirring speed regulating switch 20 for controlling the rotating speed of the electric motor 9 and a heating thermostatic switch 21 for controlling the work of the heating plate 4 are provided outside the electric cabinet 16 to facilitate the clinician's operation.

As shown in FIG. 3 and in combination with FIG. 1, the washing bottle 1, the heating plate 4, the heat insulation pad 5, the locating block 6, the permanent magnet 7, the supporting frame 8 and the electric motor 9 etc. can be arranged in the same housing 13. The bottom of the washing bottle 1 is directly supported by the heating plate 4 and the liquid delivery pipe 2 is extended from the housing 13. The arrangement of the heating plate 4, the heat insulation pad 5, the locating block 6, the permanent magnet 7, the supporting frame 8, and the electric motor 9 is the same as the arrangement that is located within the base. Herein unnecessary details will not be given. The installations of the first temperature sensor 11, the second temperature sensor 12 and the magnetic inducting block 10 are not changed.

Embodiment 2

Figure 4:
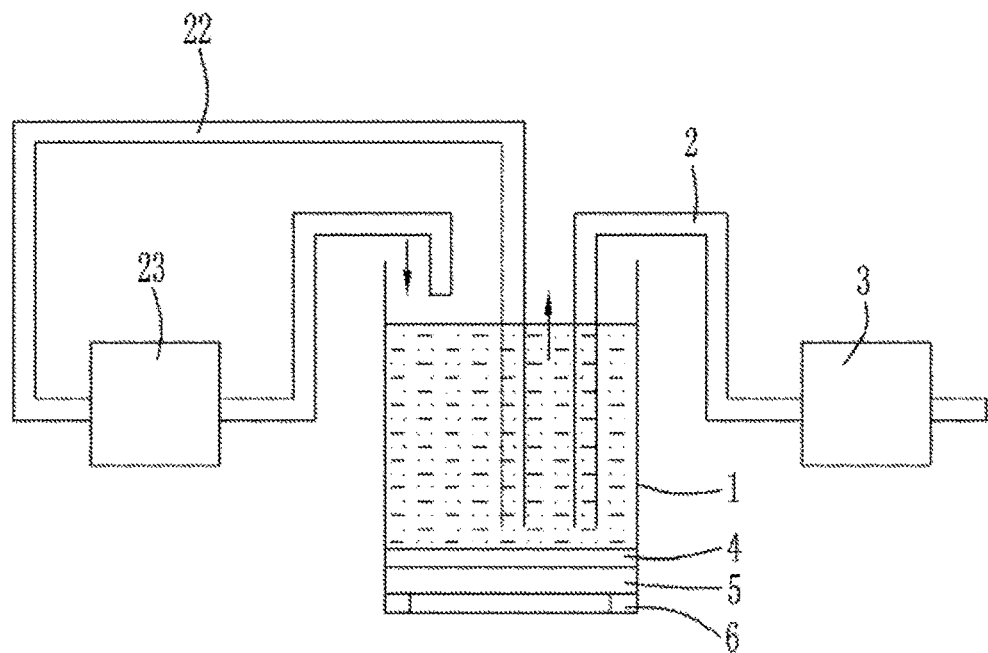
FIG. 4 is a schematic view of the structure of the stirring and heating subsystem in the second embodiment.

As shown in FIG. 4, a liquid delivery pipe 2 is connect to the washing bottle 1, extended from the washing bottle 1 and through the first peristaltic pump 3. The exit of the liquid delivery pipe 2 is connected to the inflow system of the gastrointestinal endoscope or directly connected to the observation window of the gastrointestinal endoscope. The arrangement of the first peristaltic pump 3 and the way of control are same as that in embodiment 1. Herein unnecessary details will not be given. An accommodating space is arranged below the washing bottle 1 or at the bottom of the washing bottle 1. A heating plate 4 is arranged within the accommodating space and is supported by the heat insulation pad 5. The heat insulation pad 5 is fixed to the locating block 6 within the accommodating space. The washing liquid within the washing bottle 1 can be heated when the heating plate 4 is connected to the power and can be maintained in a temperature range adapted to the human body by the temperature controller and control circuit.

As shown in FIG. 4, a second peristaltic pump 23 is provided outside the washing bottle 1 and a circulating tube passes over the second peristaltic pump 23. The liquid inlet and the liquid outlet of the circulating tube 22 are both located within the washing bottle 1, wherein the liquid inlet is near the bottom of the washing bottle 1 and the liquid outlet is near the opening of the bottle. The washing liquid within the washing bottle 1 can be pumped out via the working second peristaltic pump 23. The washing liquid within the washing bottle can be mixed evenly by the eddy formed by the power generated by the flow of the washing liquid itself, which avoids the cross contamination, meanwhile makes the washing liquid to be heated evenly.

Embodiment 3

Figure 5:
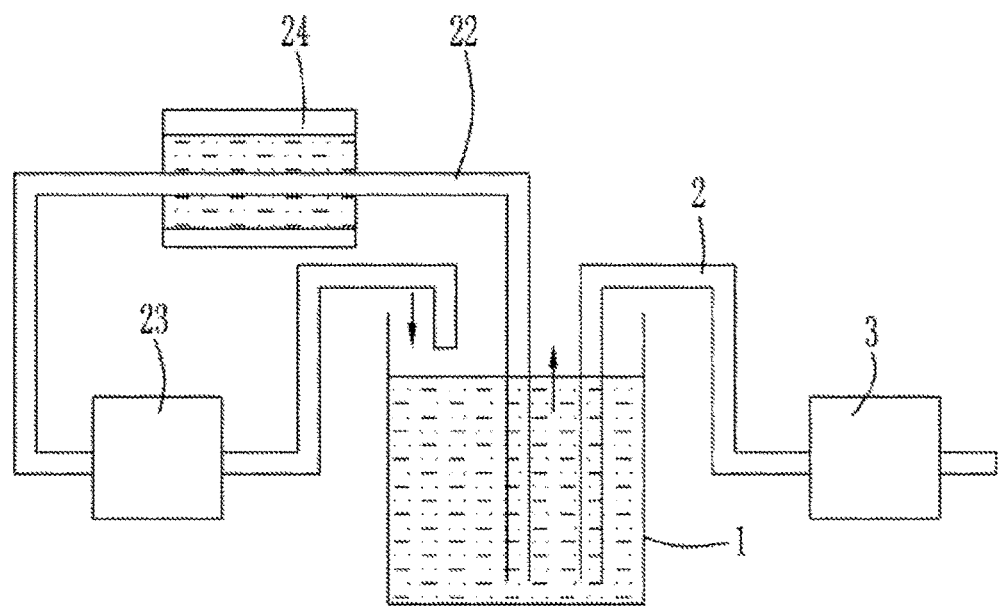
FIG. 5 is a schematic view of the structure of the stirring and heating subsystem in the third embodiment.

As shown in FIG. 5, a liquid delivery pipe 2 is connect to the washing bottle 1 and is extended from the washing bottle 1 through the first peristaltic pump 3. The exit of the liquid delivery pipe 2 is connected to the inflow system of the gastrointestinal endoscope or directly connected to the observation window of the gastrointestinal endoscope. The arrangement of the first peristaltic pump 3 and the way of control are same as that in embodiment 1. Herein unnecessary details will not be given.

As shown in FIG. 5, a second peristaltic pump 23 and a thermostatic water bath heating means 24 are provided outside the washing bottle 1. The circulating tube 22 passes through the thermostatic water bath heating means 24, and then passes through the second peristaltic pump 23. The liquid inlet and the liquid outlet of the circulating tube 22 are both located within the washing bottle 1, wherein the liquid inlet of the circulating tube 22 is near the bottom of the washing bottle 1 and the liquid outlet of the circulating tube 22 is near the opening of the bottle.

The uniform stir and mix described in the embodiment 3 still adopts the second peristaltic pump 23, which avoids the contamination of the washing liquid. The embodiment 3 adopts thermostatic water bath heating means and heats the circulating tube 22 by thermostatic water bath. The heat is conducted to the washing liquid by the circulating tube 22 so as to control the temperature of the washing liquid within the washing bottle 1. By way of water bath, the heating way is more moderate thus the temperature fluctuation range is small. In addition, because the water bath heating is conducted outside the washing bottle, the structure of the washing bottle is simpler.

Embodiment 4

Figure 6:
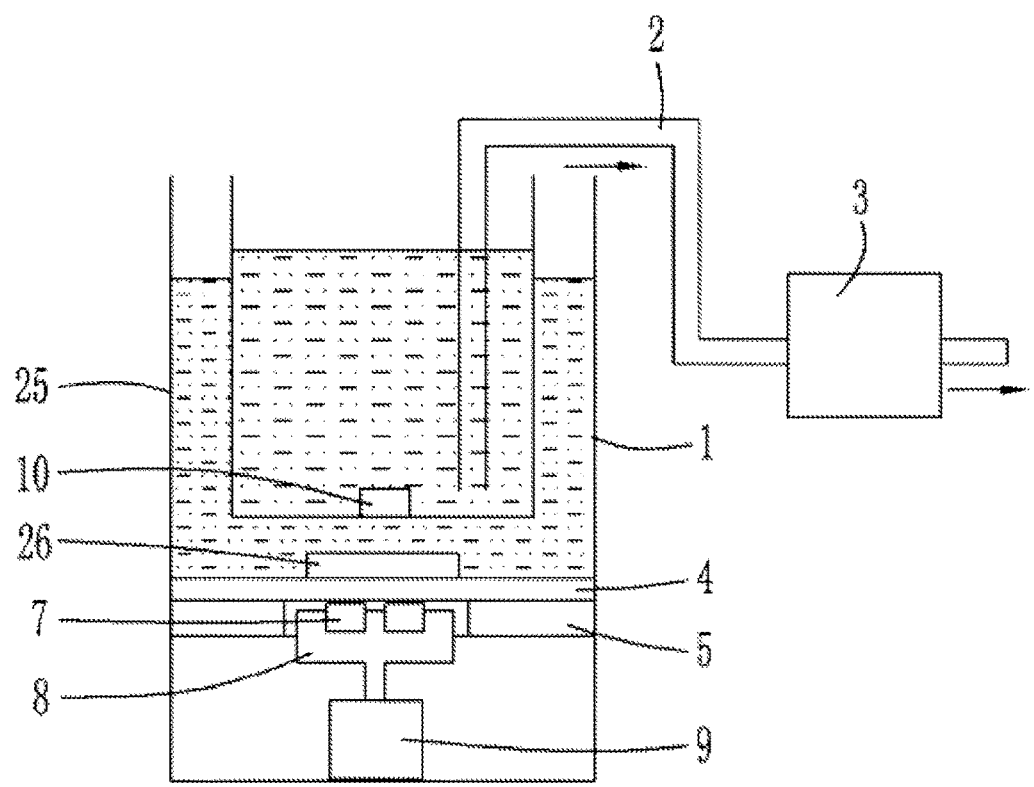
FIG. 6 is a schematic view of the structure of the stirring and heating subsystem in the fourth embodiment.

As shown in FIG. 6, a liquid delivery pipe 2 is connect to the washing bottle 1 and is extended from the washing bottle 1 through the first peristaltic pump 3. The exit of the liquid delivery pipe 2 is connected to the inflow system of the gastrointestinal endoscope or directly connected to the observation window of the gastrointestinal endoscope. The arrangement of the first peristaltic pump 3 and the way of control are same as that in embodiment 1. Herein unnecessary details will not be given. A water bath heating vessel 25 is installed in the washing bottle 1 and a magnetic inducting block 10 is fixedly installed in the center of the bottom of the washing bottle 1. A magnetic inductor 26 is installed in the center of the bottom of the water bath heating vessel and a heating plate 4 supported by the heat insulation pad 5 is disposed below the magnetic inductor 26. In the center of the heat insulation pad 5 an accommodating hole is provided in which a permanent magnet 7 is provided. The permanent magnet 7 is installed on the supporting frame 8, the lower end of which is connected to the output shaft of the electric motor 9.

Embodiment 4 adopts the water bath heating which is able to diminish the temperature fluctuation of the washing liquid. The even mixture of the washing liquid is achieved by the magnetic stir. A magnetic inductor is provided in the water bath such that the liquid in the water bath heater can be stirred and mixed evenly. Therefore, the water bath temperature outside the whole washing bottle is all around consistent and the heat conduction is kept uniform. The magnetic inductor in the water bath heating vessel and the magnetic inducting block in the washing bottle can be moved simultaneously by the drive of the same permanent magnet, hence the structure is simple.

Embodiment 5

Figure 7:
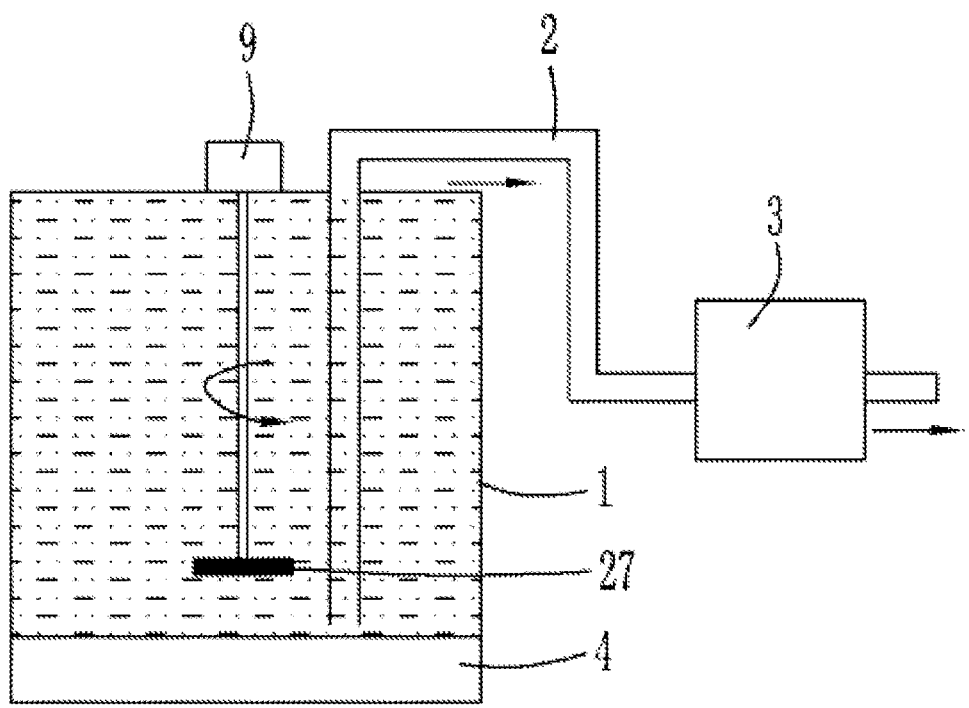
FIG. 7 is a schematic view of the structure of the stirring and heating subsystem in the fifth embodiment.

As shown in FIG. 7, a liquid delivery pipe 2 is connect to the washing bottle 1 and is extended from the washing bottle 1 through the first peristaltic pump 3. The exit of the liquid delivery pipe 2 is connected to the inflow system of the gastrointestinal endoscope or directly connected to the observation window of the gastrointestinal endoscope. The arrangement of the first peristaltic pump 3 and the way of control are same as that in embodiment 1. Herein unnecessary details will not be given. A heating plate 4 is installed at the bottom of the washing bottle 1 and is spaced apart from the washing liquid in the washing bottle. The washing liquid can be heated when the heating plate is connected to the power. A stirring paddle 27 connected to the output shaft of the electric motor 9 may be provided within the washing bottle 1. The electric motor 9 is provided over the washing bottle 1 and the output shaft of the electric motor 9 is oriented downwardly in the vertical direction. When the electric motor 9 works, the stirring paddle 27 is driven to rotate by the electric motor 9, hence stirs the washing liquid.

Embodiment 6

Figure 8:
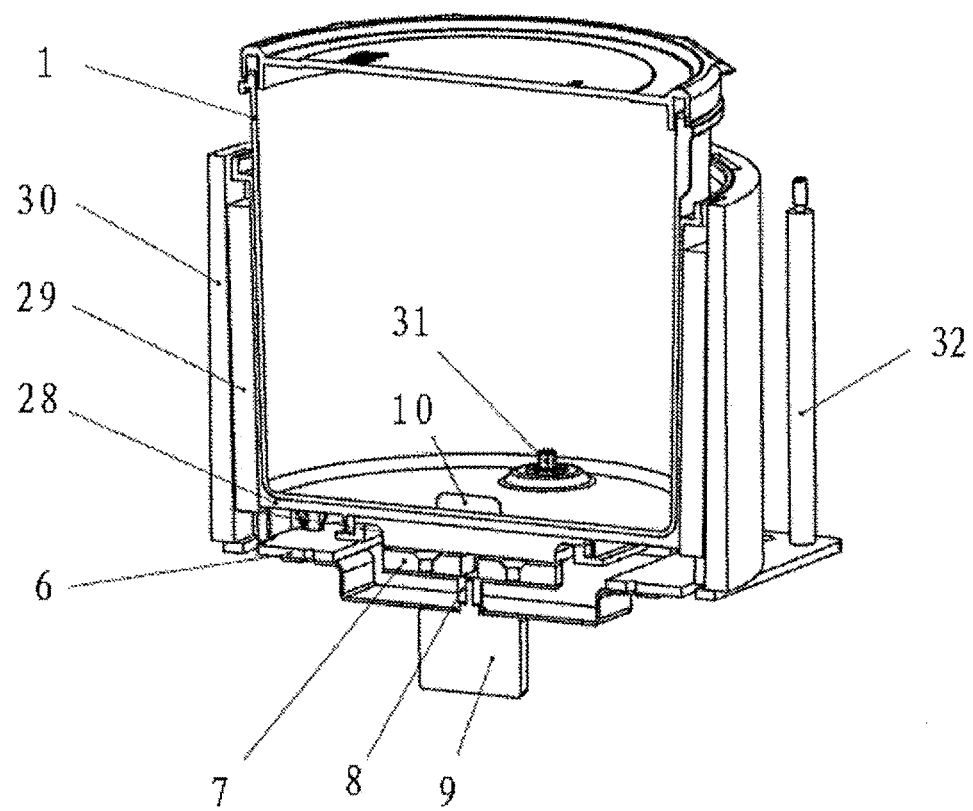
FIG. 8 is a schematic view of the structure of the stirring and heating subsystem in the sixth embodiment.

As shown in FIG. 8, the stirring and heating subsystem in the present embodiment includes a heating cup 28, a PTC heater 29, a locating block 6, a permanent magnet 7, a supporting frame 8, an electric motor 9 and a magnetic inducting block 10. The heating cup 28 is located below the washing bottle 1 and the PTC heaters 29 are fixed at the bottom of the heating cup 28 and surrounding the heating cup 28. The heat preservation layer 30 is wrapped around the FTC heater 29 and the heating cup 28 is fixed on the locating block 6. In the center of the locating block 6, an accommodating hole is provided in which two permanent magnets 7 are arranged symmetrically. Both of the two permanent magnets 7 are embedded in the upper part of the supporting frame 8 and the lower part of the supporting frame 8 is connected to the output shaft of the electric motor 9. A magnetic inducting block 10 cooperating with the permanent magnet 7 is provided over the permanent magnet 7 and is installed in the center of the bottom of the washing bottle 1. The washing bottle 1 is installed inside the heating cup 28.

A temperature sensor 31 is provided within the washing bottle 1 and is fixed to the bottom of the washing bottle 1.

In the present embodiment, the washing bottle 1, the heating cup 28, the PTC heater 29, the heat preservation layer 30, the locating block 6, the permanent magnet 7, the supporting frame 8 and the electric motor 9 are located within the same housing 13 and the liquid delivery pipe 2 is extended from the housing 13. The heating cup 28, the PTC heater 29, the heat preservation layer 30, the locating block 6, the permanent magnet 7, the supporting frame 8 and the electric motor 9 are connected to the housing 13 by the supporting shaft 32 and the washing bottle 1 is installed in the heating cup 28.

This embodiment distinguishes itself from embodiment 1 in that the heating means are different. Embodiment 1 employs the heating plate as the heating means, whereas the present embodiment employs the heating cup as the heating means. The arrangement of other position relation and the control ways are same as that of embodiment 1. Herein unnecessary details will not be given.

Embodiment 7

Figure 9:
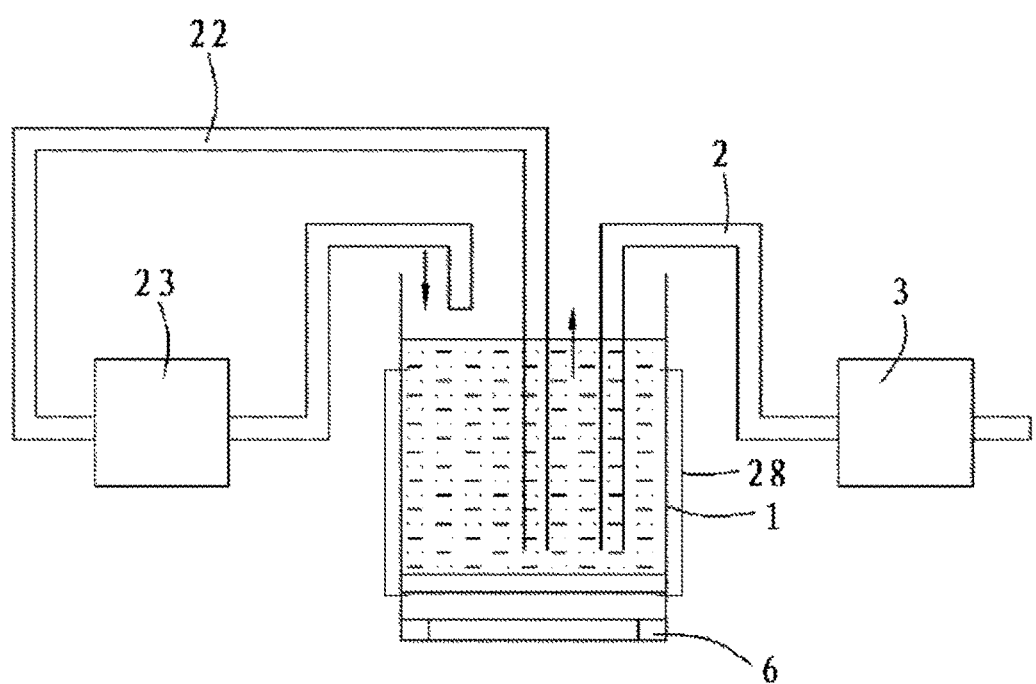
FIG. 9 is a schematic view of the structure of the stirring and heating subsystem in the seventh embodiment.

As shown in FIG. 9, the stirring and heating subsystem in the present embodiment includes a heating cup 28, a PTC heater 29, a locating block 6, a second peristaltic pump 23 and a circulating tube 22. The washing bottle 1 is located within the heating cup 28. The PTC heaters 29 are fixed at the bottom of the heating cup 28 and surrounding the heating cup 28. The heat preservation layer 30 is wrapped around the PTC heater 29 and the heating cup 28 is fixed on the locating block 6.

A second peristaltic pump 23 is provided outside the washing bottle 1. The circulating tube 22 extends from the washing bottle 1 and passes through the second peristaltic pump 23. The liquid inlet and the liquid outlet of the circulating tube 22 are both located within the washing bottle 1, wherein the liquid inlet is near the bottom of the washing bottle 1 and the liquid outlet is near the opening of the bottle.

Embodiment 8

A view definition enhancement method for gastrointestinal endoscope diagnosis and treatment utilizing the system according to any one of the embodiments 1-7 is performed in accordance with the following steps:

1) When the gastrointestinal endoscope diagnosis and treatment is conducted, add 1000-2000 ml washing liquid composed of the washing agent A and the solvent into the washing bottle 1. The washing agent A is composed of dimeticone or simethicone and glucose, wherein glucose is 15-250 parts, dimeticone or simethicone is 1-20 parts. The ratio between the mass (g) of the dimeticone or simethicones in the washing agent A and the volume (ml) of the solvent is 0.01-1%. The solvent may be saline or sterile water or glucose injection with the concentration of 5%.

Preferably, in the present embodiment, the ratio between the mass (g) of the dimeticone or simethicones in the washing agent A and the volume (ml) of the solvent is 0.15% and the volume of the washing liquid is 1000 ml. The solvent according to the present embodiment employs the saline with a concentration of 0.9%. Within this mixing ratio of the washing agent A and the solvent, the defoaming ability and speed can be ensured and the mixing time of the washing agent A can be saved. The average mixing time is 30 seconds. The washing agent A can be mixed as follows:

| Component/weight (unit: mg) | | | | | |
| --- | --- | --- | --- | --- | --- |
| Dimeticone | 20 | 40 | 80 | 120 | 400 |
| Simethicone | 300 | 550 | 900 | 1400 | 5000 |

Or

| Component/weight (unit: mg) | | | | | |
| --- | --- | --- | --- | --- | --- |
| Simethicone | 20 | 40 | 80 | 120 | 400 |
| glucose | 300 | 550 | 900 | 1400 | 5000 |

The above ratio between the dimeticone or simethicone and glucose is selected after a series of tests. In the case that no new auxiliary material is added, because dimeticone or simethicone is oily liquid, when preparing the mixture of the dimeticone or simethicone and glucose, the following result can be selected by the test. In the above ratio, the simethicone or dimeticone is heated to about 90° C. The heated simethicone or dimeticone as a binder is slowly added into glucose for high-speed stirring granulation and passes through 80 mesh sieves. After mixing it evenly, the mixture can be obtained.

2) Switch on the stirring and heating subsystem as mentioned in any one of the embodiments 1-4, at the time that the washing liquid in the washing bottle 1 is heated by the stirring and heating subsystem, stir the washing liquid within the washing bottle 1 to mix the washing liquid evenly.

3) Keep the temperature of the washing liquid in the washing bottle 1 to be maintained at 38° C. This step can be achieved by the temperature controller and the control circuit.

4) Turn on the switch of first peristaltic pump 3 to make the first peristaltic pump 3 pump out the washing liquid in the washing bottle 1. The washing liquid flows to the observation window of the gastrointestinal endoscope through the liquid delivery pipe 2 washing the location for therapy in the patient's body under observation. The flow rate does not exceed 900 ml/min. It can be seen from the observation window that when the location for therapy comes into the contact with the washing liquid, the foam is eliminated within 1-3 seconds. The observation window becomes quite clear and has no blind angle of view. The operating time for gastrointestinal endoscope inspection including the time introducing in the gastrointestinal endoscope and removing the gastrointestinal endoscope decreases from the typical 12-15 minutes to 5-9 minutes, which dramatically diminishes the time for therapy and improves the compliance and comfort of the patient.

Embodiment 9

A view definition enhancement method for gastrointestinal endoscope diagnosis and treatment utilizing the system according to any one of the embodiments 1-7 performs in accordance with the following steps:

1) The patient takes a pack of washing agent B with water 30 minutes before the gastrointestinal endoscope diagnosis and treatment begins. The washing agent B is composed of dimeticone or simethicone and glucose, wherein glucose is 15-250 parts, dimeticone or simethicone is 1-20 parts. The content range of dimeticone or simethicone in a pack of washing agent B is 40 mg-500 mg. The washing agent B can be mixed as follows:

| Component/weight (unit: mg) | | | | | |
| --- | --- | --- | --- | --- | --- |
| Dimeticone | 20 | 40 | 80 | 120 | 400 |
| glucose | 300 | 550 | 900 | 1400 | 5000 |

Or

| Component/weight (unit: mg) | | | | | |
| --- | --- | --- | --- | --- | --- |
| Simethicone | 20 | 40 | 80 | 120 | 400 |
| glucose | 300 | 550 | 900 | 1400 | 5000 |

2) When the gastrointestinal endoscope diagnosis and treatment is conducted, add 2000 ml washing liquid composed of the washing agent A and the solvent into the washing bottle 1. The washing agent A is composed of dimeticone or simethicone and glucose, wherein glucose is 15-250 parts, dimeticone or simethicone is 1-20 parts. The ratio between the mass (g) of the dimeticone or simethicones in the washing agent A and the volume (ml) of the solvent is 0.01-1%. The solvent may be saline or sterile water or pure water.

Preferably, in the present embodiment, the ratio between the mass (g) of the dimeticone or simethicones in the washing agent A and the volume (ml) of the solvent is 0.15%. The solvent according to the present embodiment employs the sterile water. The washing agent A can be mixed as follows:

| Component/weight (unit: mg) | | | | | |
| --- | --- | --- | --- | --- | --- |
| Dimeticone | 20 | 40 | 80 | 120 | 400 |
| glucose | 300 | 550 | 900 | 1400 | 5000 |

Or

| Component/weight (unit: mg) | | | | | |
|---|---|---|---|---|---|
| Simethicone | 20 | 40 | 80 | 120 | 400 |
| glucose | 300 | 550 | 900 | 1400 | 5000 |

3) Keep the temperature of the washing liquid in the washing bottle 1 to be maintained at 25° C. This step can be achieved by the temperature controller and the control circuit.

4) Turn on the switch of first peristaltic pump 3 to make the first peristaltic pump 3 pump out the washing liquid in the washing bottle 1. The washing liquid flows to the observation window of the gastrointestinal endoscope through the liquid delivery pipe 2, and washes the location for therapy in the patient's body for observation. The flow rate does not exceed 140 ml/min. It can be seen from the observation window that when the location for therapy comes into the contact with the washing liquid, the foam is eliminated within 1-3 seconds. The observation window becomes quite clear and has no blind angle of view. Because the patient took the washing agent B 30 minutes before the gastrointestinal endoscope diagnosis and treatment, the bubble or foam at the location for therapy decreases obviously, the number required for washing during the gastrointestinal endoscope diagnosis and treatment decreases. The operating time for gastrointestinal endoscope inspection according to this embodiment includes that the time for introducing and removing the gastrointestinal endoscope is shorten to 3-5 minutes, which dramatically diminishes the time for therapy and improves the compliance and comfort of the patient.

Embodiment 10

The present embodiment distinguishes itself from the embodiment 9 in that the patient takes a pack of washing agent B with water 15 minutes before the gastrointestinal endoscope diagnosis and treatment begins. The ratio between the mass (g) of the dimeticone or simethicones in the washing agent A and the volume (ml) of the solvent is 0.01%. The solvent is pure water and the temperature of the washing liquid is kept at 30° C.

Embodiment 11

The present embodiment distinguishes itself from the embodiment 9 in that the patient take a pack of washing agent B with water 20 minutes before the gastrointestinal endoscope diagnosis and treatment begins. The ratio between the mass (g) of the dimeticone or simethicones in the washing agent A and the volume (ml) of the solvent is 1%. The solvent is sterile water and the temperature of the washing liquid is kept at 30° C. The flow rate is 150 ml/min.

Description of preferably embodiments is given in combination with the accompanying drawings, but the present application does not limited to the aforementioned embodiments. The embodiments disclosed herein are exemplary but are not intended to limit the scope of the present application. Without departing the principle and scope of the claims, those skilled in the art may understand that various modifications could be made such as changing the structure of the stirring and heating subsystem, the washing bottle, the washing agent A, and the washing agent B. or installing the first peristaltic pump, washing bottle and stirring and heating subsystem in the same housing etc. Such adaptations or variations all fall into the protective scope of the present application.

INDUSTRIAL APPLICABILITY

The present application discloses a view definition enhancement system for gastrointestinal endoscope diagnosis and treatment (ESCGV), which comprises a washing bottle (1) and a liquid delivery pipe (2) led out from the washing bottle (1). The liquid delivery pipe (2) pumps washing liquid to a liquid inlet system of a gastrointestinal endoscope or an observation window of the gastrointestinal endoscope through a first peristaltic pump (3); and the washing bottle (1) is further provided with a stirring and heating subsystem capable of stirring and heating the washing liquid. In addition, the present application further discloses a view definition enhancement method for gastrointestinal endoscope diagnosis and treatment. Employing said technical solutions, the present application can improve the treatment quality of the gastrointestinal endoscope, dramatically diminishes the time for therapy and improves the compliance and comfort of the patient. In addition, when making a diagnosis and treatment for each patient, it can enhance the view definition under the gastrointestinal endoscope so as to reduce the missed diagnosis and erroneous diagnosis, and improve the treatment quality of the gastrointestinal endoscope. The present application is of high industrial applicability.

The invention claimed is:

1. A view definition enhancement system for gastrointestinal endoscope diagnosis and treatment, comprising a washing bottle (1) and a liquid delivery pipe (2) led out from the washing bottle (1),
wherein the liquid delivery pipe (2) pumps washing liquid via a first peristaltic pump (3) to a liquid inlet system of a gastrointestinal endoscope to flow into a body of a patient or to an observation window of the gastrointestinal endoscope to wash the observation window,
wherein the washing bottle (1) is provided with a stirring and heating subsystem to stir and heat the washing liquid, the stirring and heating subsystem including a heating plate (4), a heat insulation pad (5), a locating block (6), two permanent magnets (7), a supporting frame (8), an electric motor (9) and a magnetic inducting block (10),
wherein the heating plate (4) is located below the washing bottle (1) and supported by the heat insulation pad (5) which is fixed on the locating block (6),
an accommodating hole is provided in a center of the heat insulation pad (5) and the two permanent magnets (7) are provided symmetrically in the accommodating hole in the center of the heat insulation pad (5) and the two permanent magnets (7) are embedded in an upper part of the supporting frame (8),
a lower end of the frame (8) is connected to an output shaft of the electric motor (9), and
the magnetic inducting block (10), which cooperates with the two permanent magnets (7), is provided over the two permanent magnets (7) and is installed in a center of a bottom portion of the washing bottle (1),
wherein a first temperature sensor (11) is provided near the heating plate (4), a second temperature sensor (12) is provided in the washing bottle (1) and a top part of the second temperature sensor (12) is fixed to a bottle cap of the washing bottle (1), the washing bottle (1), the heating plate (4), the heat insulation pad (5), the locating block (6), the two permanent magnets (7), the supporting frame (8) and the electric motor (9) are arranged in a same housing (13) and the liquid delivery pipe (2) extends from the housing (13), and the heating plate (4), the heat insulation pad (5), the locating block (6), the two permanent magnets (7), the supporting frame (8) and the electric motor (9) are arranged in a same base (14) and the washing bottle (1) is supported by the base (14) within the housing (13).

2. The view definition enhancement system for gastrointestinal endoscope diagnosis and treatment according to claim 1, wherein the washing liquid is composed of a solvent and a washing agent A, and the washing agent A comprises (i) dimeticone or simethicone and (ii) glucose, wherein glucose is 15-250 parts, and dimeticone or simethicone is 1-20 parts, and wherein the solvent is saline, sterile water, pure water, or a glucose injection, the solvent having a concentration of 5%, and a ratio between the mass of the dimeticone or simethicone and the volume of the solvent is 0.01-1% in the unit of g/ml.

3. A view definition enhancement method for gastrointestinal endoscope diagnosis and treatment utilizing the view definition enhancement system for gastrointestinal endoscope diagnosis and treatment according to claim 1, wherein said method comprises the following steps:

1) adding the washing liquid to the washing bottle (1);
2) switching on the stirring and heating subsystem to simultaneously heat and stir the washing liquid in the water bottle, stirring the washing liquid within the washing bottle mixes the washing liquid evenly;
3) maintaining the temperature of the washing liquid in the washing bottle (1) at 25-38° C.;
4) turning on a switch of the first peristaltic pump (3) to make the first peristaltic pump (3) pump out the washing liquid in the washing bottle (1), the washing liquid flowing to the liquid inlet system of the gastrointestinal endoscope or the observation window of the gastrointestinal endoscope through the liquid delivery pipe (2) and washing a location for therapy in a patient's body for observation.

4. The view definition enhancement method for gastrointestinal endoscope diagnosis and treatment according to claim 3, wherein a volume of the washing liquid is 450-2000 ml.

5. The view definition enhancement method for gastrointestinal endoscope diagnosis and treatment according to claim 3, wherein an adjustable range of a flow rate of the first peristaltic pump (3) is 0-900 ml/min, and a maximum flow rate is controlled at 900 ml/min.

6. The view definition enhancement method for gastrointestinal endoscope diagnosis and treatment according to claim 3, wherein the washing liquid is composed of a solvent and a washing agent A, and the washing agent A comprises (i) dimeticone or simethicone and (ii) glucose, wherein glucose is 15-250 parts, and dimeticone or simethicone is 1-20 parts.

7. The view definition enhancement method for gastrointestinal endoscope diagnosis and treatment according to claim 6, wherein the solvent is saline, sterile water, or a glucose injection, the solvent having a concentration of 5% and a ratio between the mass of the dimeticone or simethicone and the volume of the solvent is 0.01-1% in the unit of g/ml.

8. The view definition enhancement method for gastrointestinal endoscope diagnosis and treatment according to claim 3, administering a pack of a washing agent B to a patient 15-30 minutes before the gastrointestinal endoscope diagnosis and treatment begins, the washing agent B comprises (i) dimeticone or simethicone and (ii) glucose, wherein glucose is 15-250 parts, dimeticone or simethicone is 1-20 parts, and a content range of dimeticone or simethicone in the pack of washing agent B is 40 mg-500 mg/pack.

* * * * *